United States Patent [19]
Liotta et al.

[11] Patent Number: 5,372,809
[45] Date of Patent: Dec. 13, 1994

[54] ANTIGENIC MATRIX METALLOPROTEINASE PEPTIDES

[75] Inventors: Lance A. Liotta, Potomac; William Stetler-Stevenson, Silver Spring; Henry Krutzsch, Bethesda, all of Md.

[73] Assignee: The United States of America as represented by the Department of Health and Human Services, Washington, D.C.

[21] Appl. No.: 830,313

[22] Filed: Jan. 31, 1992

Related U.S. Application Data

[60] Division of Ser. No. 488,460, Feb. 26, 1990, Pat. No. 5,280,106, which is a continuation-in-part of Ser. No. 317,407, Mar. 1, 1989, Pat. No. 5,270,447, which is a continuation-in-part of Ser. No. 248,420, Sep. 23, 1988, abandoned, which is a continuation-in-part of Ser. No. 196,242, May 20, 1988, abandoned.

[51] Int. Cl.$^5$ .............. A61K 37/547; C07K 7/08; C07K 17/02
[52] U.S. Cl. .............. 424/185.1; 530/326; 530/806; 530/810; 930/10
[58] Field of Search .............. 530/330, 329, 328, 327, 530/326, 325, 806, 810; 514/18, 17, 16, 15, 14, 13; 435/183, 219; 930/10; 424/88

[56] References Cited

U.S. PATENT DOCUMENTS 4,677,058  6/1987  Tryggvason et al. .................. 435/7
4,923,818  5/1990  Goldberg et al. .................. 435/226

OTHER PUBLICATIONS

Murphy et al. (1985) Biochim. Biophys. Acta. 831:49–58.
Hoyhtga et al. (1988, Jun.) FEBs Lett. 233 (1):109–113.
Knauper et al. (1990, Apr.) Eur. J. Biochem. 189:295–300.
Stetler-Stevenson et al. (1989, Jan. 25) J. Biol. Chem. 264(3):1353–1356.
Collier et al. (1988, May 15) J. Biol. Chem. 263(14):6579–6587.
Lerner (1982) Nature 299:592–596.
Boyer (1986) "Modern Experimental Brochemistry", Addison-Wesley, Reading, Mass., pp. 534–535.
Hermodson et al. (1983) Methods Enzymol. 91:352–359.
Metzler (1977) "Biochemistry. The Chemical Reactions of Living Cells", Academic Press, New York, N.Y., p. 127.
Seltzer (1985) J. Chrom. 326:147–155.
McKerrow (1987, May 5) J. Biol. Chem. 262(13):5943.
Hibbs et al. (1985) J. Biol. Chem. 260(4):2493–2500.

*Primary Examiner*—Stephen G. Walsh
*Attorney, Agent, or Firm*—Townsend and Townsend Khourie and Crew

[57] ABSTRACT

A family of metalloproteinases exist which cleave extracellular matrix molecules. These metalloproteinases are secreted in a latent inactive form and require activation in order to specifically cleave the preferred substrate. A series of peptides have been prepared based on the complete sequence analysis of type IV procollagenase. Peptide inhibitors were synthesized which correspond to cysteine repeat regions and histidine containing regions; the mechanism of action of these peptides involves inhibition of binding of the enzyme to the substrate. Peptide inhibitors were synthesized which correspond to the peptide cleaved off during activation, and constitute a novel class of metalloproteinase inhibitors. These inhibitors are members of a series of peptides which contain the core amino acid sequence RKPRC or analogs thereof. The cysteine residue is required for activity. Affinity purified antibodies directed against specific peptides can be used to a) detect any general metalloproteinase enzyme with the sequence in part VAAHE or PRCGNPD, and distinguish it from other known members of the metalloproteinase family, b) block functional domains resulting in the inhibition of enzyme activity, and c) distinguish latent from activated forms of the enzyme.

6 Claims, 14 Drawing Sheets

TYPE IV PROCOLLAGENASE AMINO ACID SEQUENCE

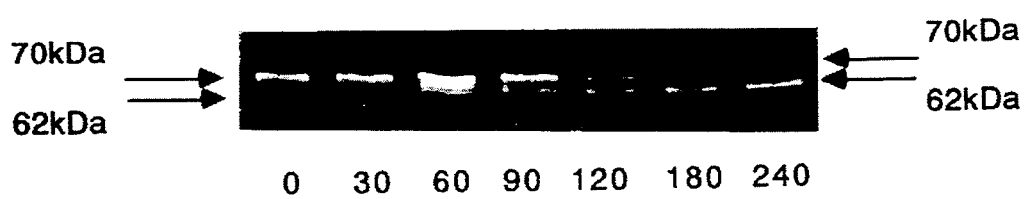
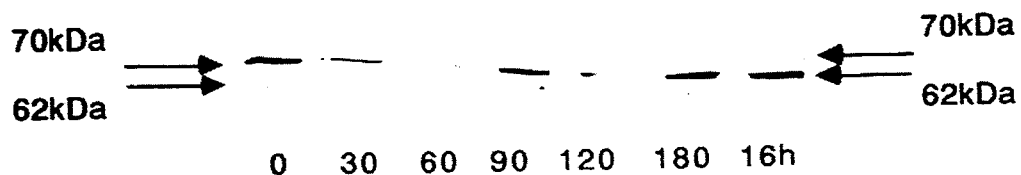
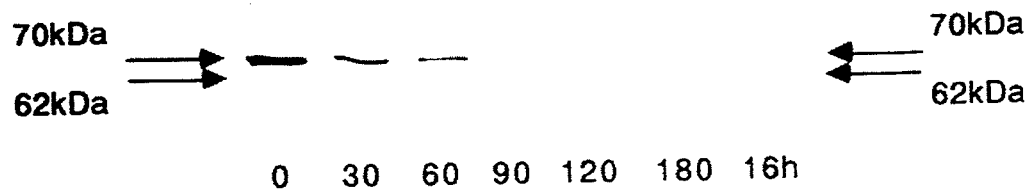
FIG. 7.

```
 1              10              20              30              40              50
APSPIIKFPGDVAPKTDKELAVQ-YLNTFYGCPKESCNLFVL-KDT----LKK---MQK
FPATLETQEQDVDLVQKYLEKYYNLKNDGRQVEKR-RNSGPVVEKLK---QMQE
YPLDGAARGEDTSMNLVQKYLENYYDLEKDVKQ-FVRRKDSGPVV---KKIREMQK 60              70              80              90             100             110
FFGLPQTGDLDQNTIETMRK|PRCGNPDV|AN|Y|NFFPPRKPKWDKNQITYRIIGYTPDLDPET
FFGLKVTGKPDAETLKVMKQ|PRCGVPDV|AQ|F|VLTEGNPRWEQTHLRYRIENYTPDLPRAD
FLGLEVTGKLDSDTLEVMRK|PRCGVPDV|GH|F|RTFPGIPKWRKTHLTYRIVNYTPDLPKDA
                         A       B

FIG. 10.
```

```
1         10        20         30         40                    50
APSPIIKFPGDVAPKTDKELAVQ-YLNTFYGCPKESCNLFVL-KDT------LKK---MQK

APSPIIKFPGDVAPKTDK  NOT ACTIVE

ELAVQYLNTFYGCPK  NOT ACTIVE 60        70        80         90         100       110
FFGLPQTGDLDQNTIE|TMRKPRCG|NPDVANYNFFPRKPKWDKNQITYRIIGYTPDLDPET
                         NPDVANYNFFPRKPKWDKNQ  NOT ACTIVE
                 TMRKPRCGNPDVANYNFFPRKPK  ACTIVE
                 TMRKPRCGN PDVAN  ACTIVE
```

FIG. 12.

SEQUENCE RANGE: 1 TO 240

```
GCG CCG TCG CCC ATC AAG TTC CCC GGC GAT GTC GCC CCC AAA ACG GAC
 A   P   S   P   I   K   F   P   G   D   V   A   P   K   T   D >
                                                              100
                                                               *
AAA GAG TTG GCA GTG CAA TAC CTG AAC ACC TTC TAT GGC TGC CCC AAG GAG
 K   E   L   A   V   Q   Y   L   N   T   F   Y   G   C   P   K   E >

AGC TGC AAC CTG TTT GTG CTG AAG GAC ACA CTA AAG AAG ATG CAG AAG TTC
 S   C   N   L   F   V   L   K   D   T   L   K   K   M   Q   K   F >
                                                              200
                                                               *
TTT GGA CTG CCC CAG ACA GGT GAT CTT GAC CAG AAT ACC ATC GAG ACC ATG
 F   G   L   P   Q   T   G   D   L   D   Q   N   T   I   E   T   M >

CGG AAG CCA CGC TGC GGC AAC CCA GAT GTG GCC AAC
 R   K   P   R   C   G   N   P   D   V   A   N >
```

FIG. 13.

ANTIGENIC MATRIX METALLOPROTEINASE PEPTIDES

This is a division of application Ser. No. 07/488,460, filed Feb. 26, 1990, now U.S. Pat. No. 5,280,106, which is a continuation-in-part of application Ser. No. 07/317,407, filed Mar. 1, 1989, now U.S. Pat. No. 5,270,447, which is a continuation-in-part of application Ser. No. 07/248,420, filed Sep. 23, 1988, now abandoned, which is a continuation-in-part of application Ser. No. 07/196,242, filed May 20, 1988, now abandoned.

BACKGROUND OF THE INVENTION

1. Field of the Invention

This invention relates to peptides useful in metalloproteinase detection and inhibition. Specifically, the invention relates to peptides derived from the sequence of type IV collagenase which correspond to domains of the enzyme which are involved in activation of the enzyme and interaction of the enzyme with its substrate. Antibodies recognizing the peptides are useful in enzyme detection. Specific peptides, identified by means of functional studies, constitute new classes of metalloproteinase inhibitors.

2. Background

The degradation of interstitial and basement membrane collagens is initiated by a specific class of metalloproteinase, the matrix metalloproteinases, also known as the collagenases (EC 3.4.24.7), which are secreted into the extracellular matrix in zymogen form. Members of this collagenase gene family include: the interstitial collagenases, which degrade collagen types I, II and III and have been characterized with respect to substrate specificity and requirements for activation (Stricklin, G. P., Jeffrey, J. J., Rosewit, W. T., and Eisen, A. Z., 1983, *Biochemistry* 22, 61-68; Goldberg, G. I., Wilhlem, S., Kronberger, A., Bauer, E. A., Grant, G. A., and Eisen, A. Z., 1986, *J. Biol. Chem.* 261, 6600-6605; Hasty, K. A., Jeffrey, J. J., Hibbs, M. S., and Welgus, H. G., 1987, *J. Biol. Chem.* 262, 10048-1052; Fields, G. B., Van Wart, H. E., and Birkedal-Hansen, H., 1987, *J. Biol. Chem.* 262, 6221-6226; Grant, G. A., Eisen, A. Z., Mariner, B. L. Rosweit, W. T., and Goldberg, G. I., 1987, *J. Biol. Chem.* 262, 5886-5889); stromelysin, which degrades proteoglycans, glycoproteins, and the non-helical portions of collagenous molecules (Wilhelm, S. M., Collierm, I. E., Kronberger, A., Eisen, A. Z., Marmer, B. L., Grant, G. A., Bauer, E., and Goldberg, G. I., 1987, *Proc. Natl. Acad. Sci. U.S.A.* 84, 6725-6729; Whitman, S. E., Murphy, G., Angel, P., Rahmsforf, H. J., Smith, B. J., Lyons, A., Harris, T. J. T., Reynolds. J. J., Herrlich, P. and Docherty, A. J. P., 1986, *Biochem. J.* 240, 913-916); and type IV collagenase, which degrades pepsin-resistant triple-helical type IV collagen and interstitial collagens (gelatin). Type IV collagenase has been identified in human tumor cells (Liotta, L. A., Kleinerman, J., Catanzaro, P., and Rynbrandt, D., 1977, *J. Natl. Cancer Inst.* 58, 1427-1439; Turpeenniemi-Hujanen, T., and Tryggvason, K., 1982, *Int. J. Cancer* 30p, 669-673; Liotta, L. A., Abe, S., Gehron-Robey, P., and Martin, G. R., 1979, *Proc. Natl. Acad. Sci. U.S.A.* 76 2268-2272; Liotta, L. A., Tryggvasson, K., Garbisa, S., Hart, I., Foltz, C. M., and Shafie, S., 1980, *Nature, Lond.*, 284, 67-68; Collier, I. E., Wilhelm, S. M., Eisen, A. Z., Mariner, B. L., Grant, G. A., Seltzer, J. L., Kronberger, A., He., C., Bauer, E. A., and Goldberg, G. I., 1988, *J. Biol. Chem.* 263, 6579-6587), endothelial cells (Kalebic, T., Barbisa, S., Glaser, B., and Liotta, L. A., 1983, *Science* 221, 281-283), bone (Murphy, G., McAlpine, C. G., Poll, C. T., and Reynolds, J. J., 1985, *Biochem. Biophys. Acta* 831, 49-58), fibroblasts (Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, *J. Biol. Chem.* 263, 6579-6587), polymorphonuclear leukocytes (Uitto, V. J., Schwartx, D., and Veis, A., 1980, *Eur. J. Biochem.* 105, 409-417) and macrophages (Garbidsa, S., Ballin, M., Daga-Giordini, D., Fastelli, G., Naturale, M., Negro, A., Semenzato, G., and Liotta, L. A., 1986, *J. Biol. Chem.* 261, 2369-2375). This enzyme is a neutral metalloproteinase of 68 to 72 kilodaltons which is secreted in zymogen form (Liotta, L. A., Abe, S., Gehron-Robey, P., and Martin, G. R., 1979, *Proc. Natl. Acad. Sci. U.S.A.* 76, 2268-2272; Liotta, L. A., Tryggvassin, K., Garbisa, S., Gehron-Robey, P., and Abe, S., 1981, *Biochemistry* 20, 100-104; Salo, T., Liotta, L. A., and Tryggvsasson, K., 1983, *J. Biol. Chem.* 258, 3058-3063). In addition, several other members of this collagenase gene family have been described recently, including a second type of stromelysin (stromelysin-2), a 92 kilodalton form of type IV collagenase, and Putative Uterine Metalloproteinase (PUMP)-1, a low molecular weight uterine collagenase (Wilhelm, S. M., Collier, I. E., Marmer, B. L., Eisen, A. Z., Grant, G. A., and Goldberg, G. I., 1989, *J. Biol. Chem.* 264, 17213-17221; Woessner, J. F. and Talpin, C. J., 1988, *J. Biol. Chem.* 263, 16918-16925).

The 70 kilodalton type IV collagenase has been closely linked to the metastatic potential of tumors in murine tumor models (Liotta, L. A., Tryggvasson, K., Garbisa, S., Hart, I., Foltz, C. M., and Shafie, S., 1980, *Nature*, Lond, 284, 67-68) and is augmented following H-ras oncogene induced genetic induction of the metastatic phenotype (Muschel, R., Williams, J. E., Lowy, D. R., and Liotta, L. A., 1985, *Amer. J. Pathol.* 121, 1-8; Garbisa, S., Pozzatti, R., Muschel, R. J., Saffiotti, U., Ballin, M., Goldfarb, R. H., Khoury, G., and Liotta, L. A., 1987, *Cancer Res.* 47, 1523-1528). Trypsin treatment results in activation of the latent enzyme and a concomitant reduction in the molecular mass (Liotta, L. A., Tryggvasson, K., Garbisa, S., Gehron-Robery, P., and Abe, S., 1981, *Biochemistry* 20, 100-104). Organomercurial compounds have also been shown to activate this enzyme, and these are also associated with a reduction in the molecular mass (Collier, I. E., Wilhelm, S. M., Eisen, A. Z., Marmer, B. L., Grant, G. A., Seltzzer, J. L., Kronberger, A., He., C., Bauer, E. A., and Goldberg, G. I., 1988, *J. Biol. Chem.* 263, 6579-6587; Murphy, G., McAlpine, C. G., Poll, C. T., and Reynolds, J. J., 1985, *Biochem. Biophys. Acta* 831, 49-58). The activated enzyme cleaves type IV collagen to generate characteristic ¼ amino-terminal and ¾ carboxy-terminal fragments (Liotta, L. A., Tryggvasson, K., Garbis, S., Gehron-Robey, P., and Abe, S., 1981, *Biochemistry* 20, 100-104; Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, *J. Biol. Chem.* 263, 6579-6587; Fessler, L. I., Duncan, K. G., Fessler, J. H., Salo, T., and Tryggvason, K., 1984, *J. Biol. Chem.* 259, 9783-9789). It has also been demonstrated that gelatinolytic activity is associated with this enzyme (Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, *J.*

Biol. Chem. 263, 6579-6587; Hoyhtya, M., Turpeenniemi-Hujanen, T., Stetler-Stevenson, W., Krutzsch, H., Tryggvason, K., and Liotta, L. A., 1988, *FEBS Letters* 233, 109-113; Murphy, G., McAlpine, C. G., Poll, C. T., and Reynolds, J. J., 1985, *Biochem. Biophys. Acta* 831, 49-58) as well as a type V collagenolytic activity (Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, *J. Biol. Chem.* 263, 6579-6587; Murphy, G., McAlpine, C. G., Poll, C. T., and Reynolds, J. J., 1985, *Biochem. Biophys. Acta* 831, 49-58).

Type IV collagenase has been purified from human melanoma cells and sequence information on the intact protein amino terminus has been obtained as well as on tryptic and cyanogen bromide peptide fragments (Hoyhtya, M., Turpeenniemi-Hujanen, T., Stetler-Stevenson, W., Krutzsch, H., Tryggvason, K., and Liotta, L. A., 1988, *FEBS Letters* 233, 109-113). The sequence information demonstrates that type IV collagenase shows limited sequence homology to interstitial collagenase and stromelysin. A recent report has characterized a partial cDNA clone for a metalloproteinase secreted by H-ras-transformed human bronchial epithelial cells (Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, *J. Biol. Chem.* 263, 6579-6587). The transformed bronchial epithelial enzyme is capable of specifically degrading type IV collagen, and the deduced amino acid sequence shows identity with that reported for tryptic and cyanogen bromide fragments of human tumor IV collagenase (Hoyhtya, M., Turpeenniemi-Hujanen, T., Stetler-Stevenson, W., Krutzsch, H., Tryggvason, K., and Liotta, L. A., 1988, *FEBS Letters* 233, 109-113). Thus, human melanoma cell type IV collagenase appears identical with the enzyme from H-ras-transformed bronchial epithelial cells, which is also found in fibroblasts (Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, *J. Biol. Chem.* 263, 6579-6587) and bone cell explants (Murphy, G., McAlpine, C. G., Poll, C. T., and Reynolds, J. J., 1985, *Biochem. Biophys. Acta* 831, 49-58).

SUMMARY OF THE INVENTION

The complete amino acid sequence of the zymogen form of the type IV collagenase purified from human melanoma cells has now been analyzed and a series of inhibitory synthetic peptides corresponding to a variety of domains of the enzyme have been prepared. These domains include: the 80 residue amino terminus which is cleaved from the proenzyme during activation; a cysteine-rich interior domain; a histidine-containing region; and a region 159 residues from the carboxy terminus. Peptides from these domains have been used to generate antibodies against specific domains within the type IV collagenase molecule. In the present invention, the antibodies, direct amino acid sequence analysis, and peptides have been used to determine a) the region of the enzyme involved in binding and interaction with the substrate, and b) the structure of the major type IV collagenase conversion product produced during zymogen activation with the organomercurial compound p-aminophenylmercuric acetate.

It was discovered that type IV collagenase proenzyme activation by an organomercurial compound, pAPMA, is accompanied by an autocatalytic removal of an 80 amino acid amino terminal fragment, resulting in a stable, active enzyme species of 62 kDa. Furthermore, these data show that type IV collagenase shares not only sequence homology but functional domain identity with the amino terminal regions of other extracellular matrix degrading metalloproteinases.

As shown in FIGS. 8 and 9, below, an amino terminal peptide (residues 1-80) is cleaved off during type IV collagenase activation. This discovery raised the possibility that this peptide contains an intrinsic enzyme inhibitor which blocks the active site and renders the enzyme inactive. Removal of this amino terminal segment during activation thus would remove this inhibitor and exposes the active site. The critical region involved in the inhibition is the region enclosed in a box in FIG. 10 which contains an unpaired cysteine residue. This region shows a conserved nature in the other matrix metalloproteinases, and it has a high probability of beta turn conformation by Chou Fassman analysis. Furthermore, it was reasonable to hypothesize that the unpaired cysteine residue in this sequence interacted in a noncovalent fashion with the metal ion in the active site of the enzyme. Organomercurial activation (it is known that APMA binds to sulfhydryl residues) would thus disrupt this interaction and cause a conformational change which would separate the inhibitor segment from proximity to the active site. To test his completely novel hypothesis, synthetic peptides were prepared which correspond to a series of overlapping regions in the amino terminal residues 1-87. As shown in FIGS. 11 and 12 and Table 4, below, only those peptides incorporating the conserved region containing the unpaired cysteine were strongly inhibitory at concentration less than 0.1 mM. The cysteine was required for the activity. These peptides, therefore, constitute a highly novel class of inhibitors for metalloproteinases.

In summary, the discoveries stemming from this analysis have led to identification of a) a region near the amino terminus of type IV procollagenase that constitutes an intrinsic enzyme inhibitor which may block the active site of the enzyme when the enzyme is in a latent state, and b) a region near the middle of the enzyme that is involved in binding and interaction with the substrate. Peptides homologous to these regions constitute novel matrix metalloproteinase inhibitors.

DESCRIPTION OF THE DRAWINGS

FIG. 1 illustrates the complete amino acid sequence of human type IV procollagenase secreted by tumor cells.

FIG. 3 (B) ELISA characterization of antipeptide antibody A472-490. The synthetic peptide corresponding to the internal residues 472-490 of type IV procollagenase was synthesized and used as an antigen. The peptide-bovine serum albumin conjugate was used as coating antigen in this ELISA.

FIG. 3 (C) Competition ELISA assays were performed using the appropriate peptide for each antibody.

Peptide-bovine serum albumin was used as coating antigen and free peptides were used as competing antigens.

Figure 3A:
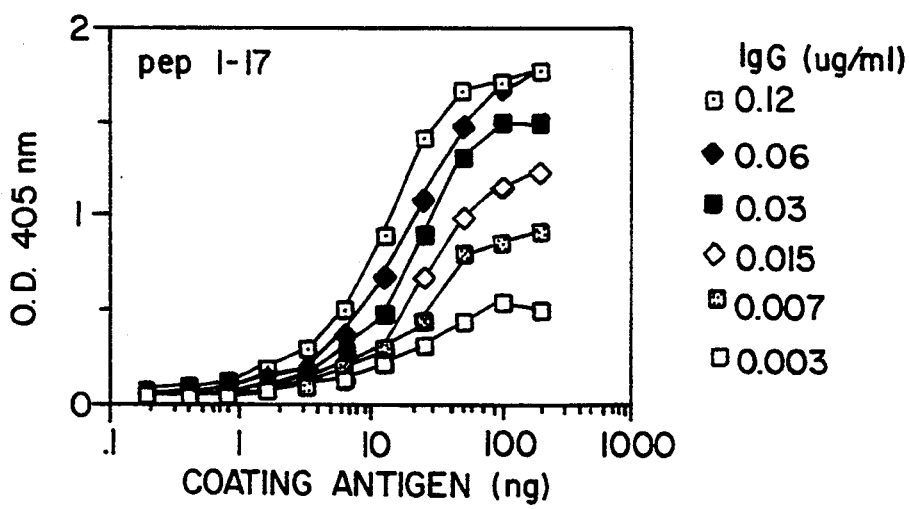
FIG. 3 (A) ELISA characterization of antipeptide antibody A1-17. The synthetic peptide corresponding to the amino terminal residues 1 through 17 of type IV procollagenase was synthesized and used an antigen. The peptide-bovine serum albumin conjugate was used as coating antigen in this ELISA.
Figure 3B:
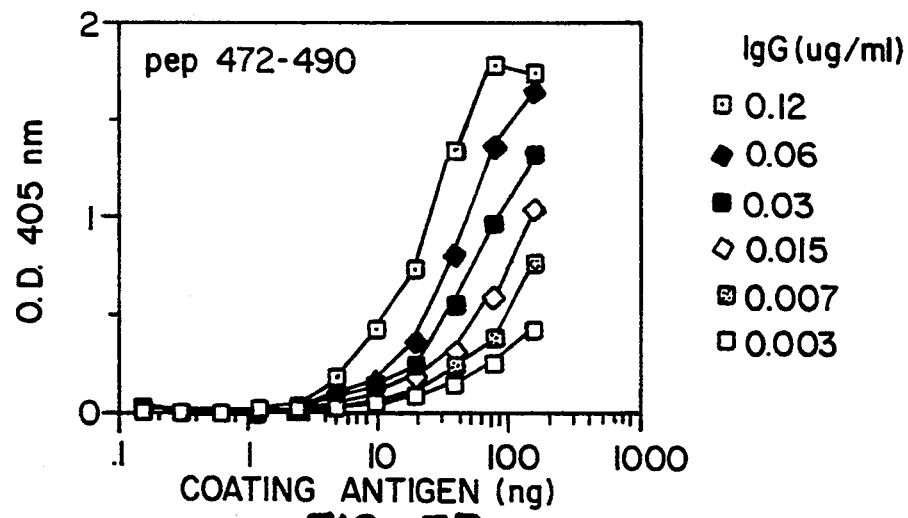
Figure 3C:
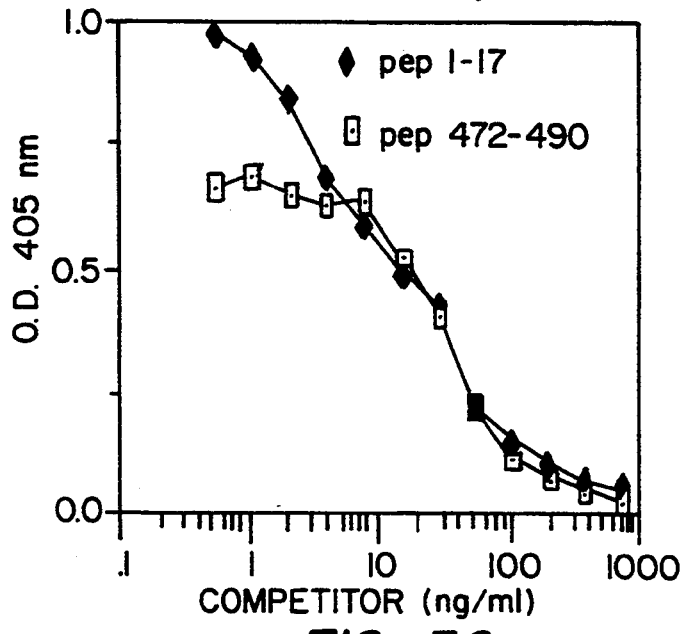

FIG. 3 (D) Western blots of crude and gelatin-affinity purified type IV procollagenase. Shown are crude type IV procollagenase immunoblotted with A1–17 (20 μl of A2058 melanoma cell conditioned media, lane a), purified type IV collagenase immunoblotted with A472–490 (30 ng, lane c).

Figure 4A:
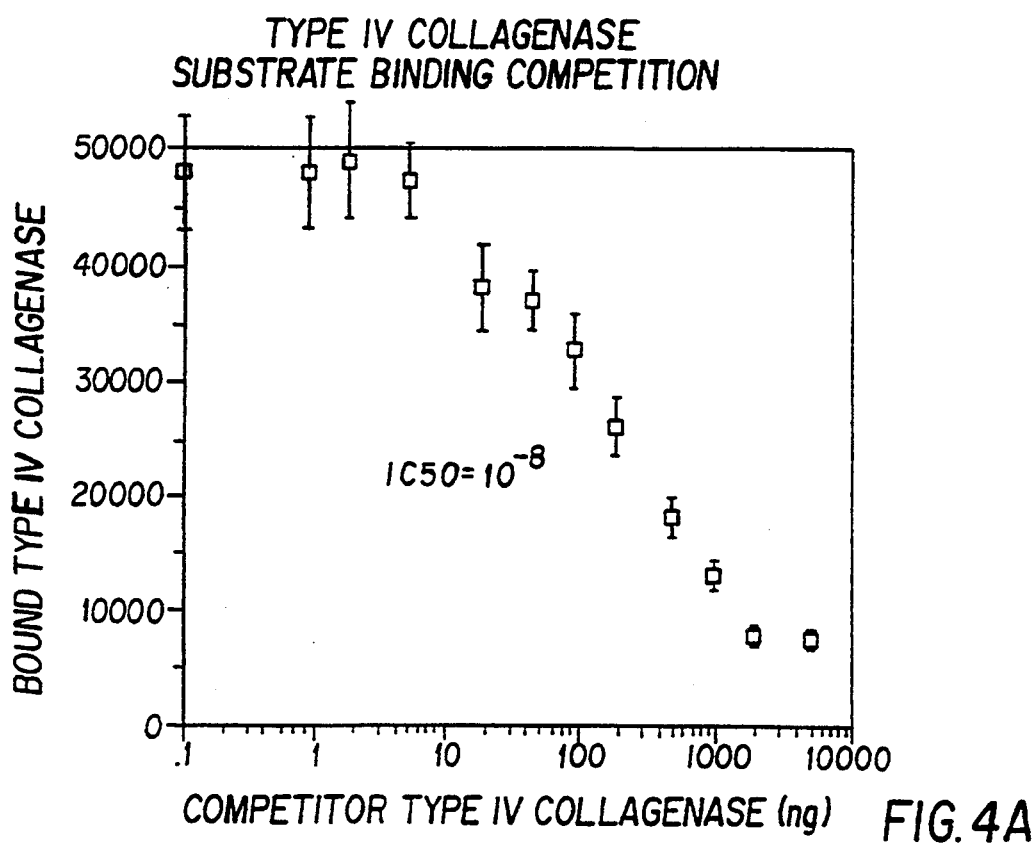
Figure 4B:
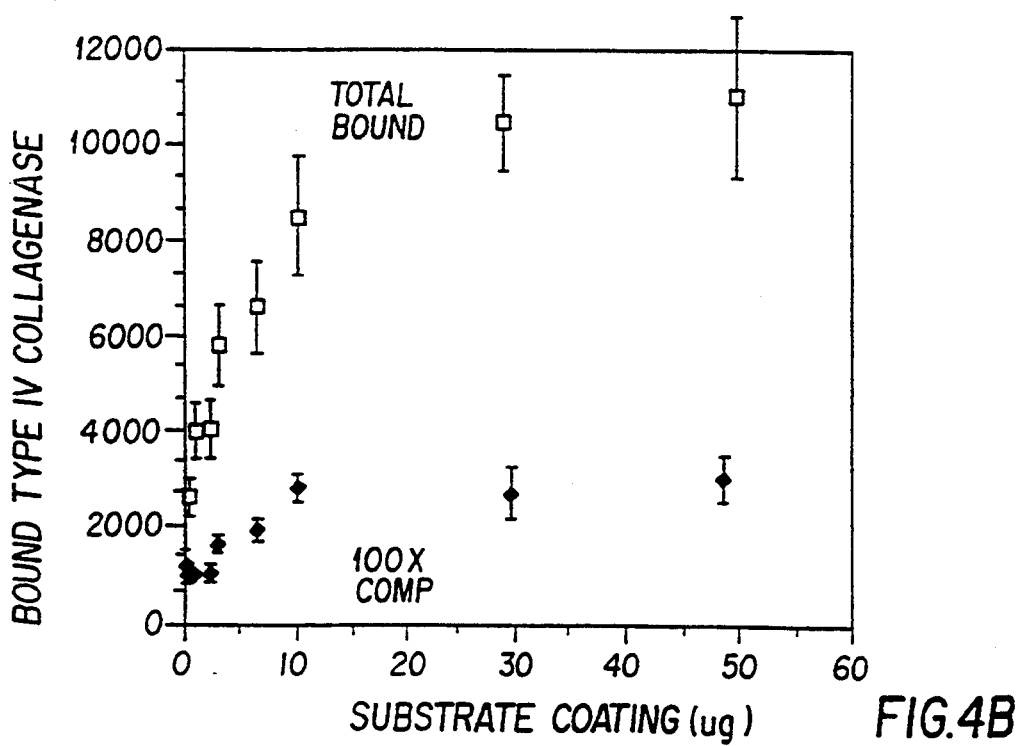

FIG. 4 illustrates the assay for type IV collagenase binding to its substrate type IV collagen. Purified type IV collagenase was used to compete for the binding of labeled type IV collagenase to pepsinized type IV collagen coated in microtiter wells (mean±S.D.). Saturation of binding is demonstrated in the lower curve using increasing amounts of substrate.

Figure 5:
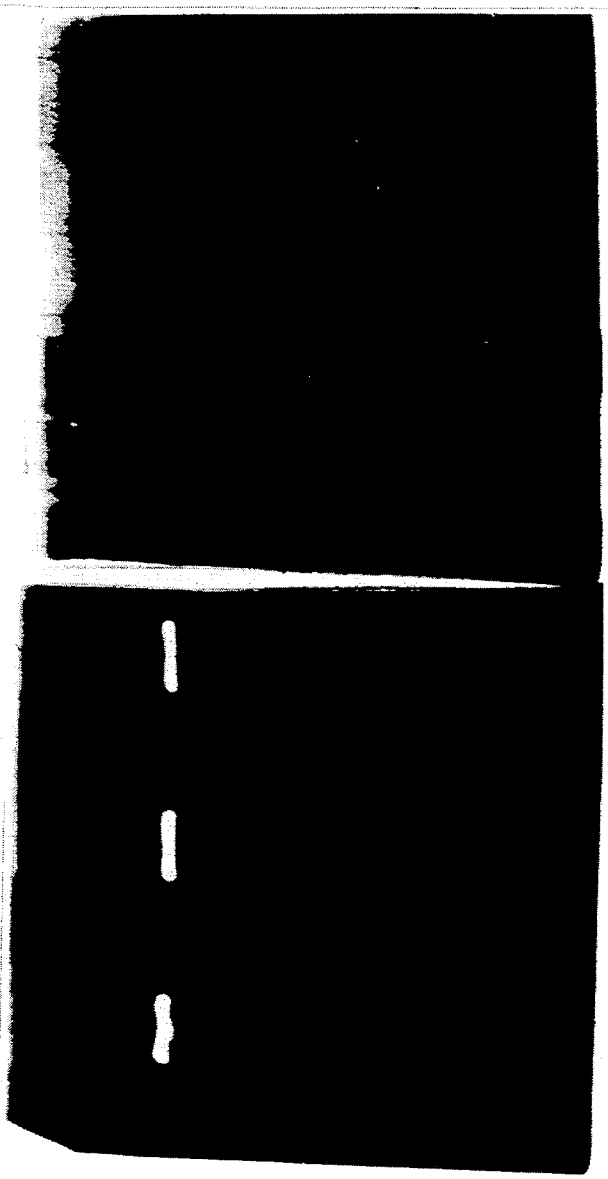

FIG. 5 illustrates the gelatin zymogram inhibition of type IV collagenase by the designated synthetic peptides. The gelatinase activity is visualized as white cleared bands at approximately 70 kDa. The white cleared bands are abolished in the presence of the inhibitor. Three replicates are shown.

Figure 6:
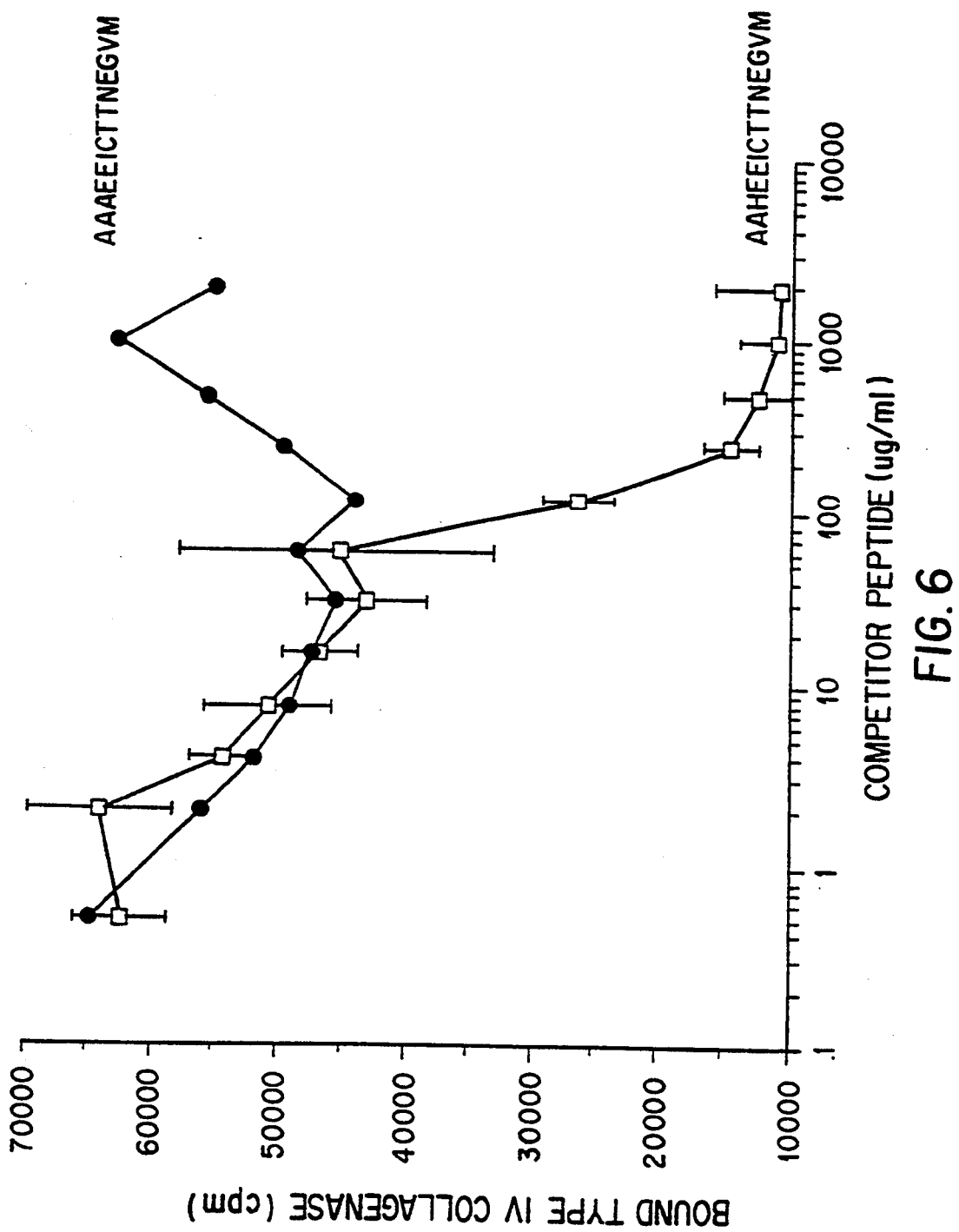

FIG. 6 illustrates an example inhibition of binding of labeled type IV collagenase to type IV collagen by the designated peptides. The histidine containing peptide is derived from a region in fibronectin homologous to the histidine containing domain of type IV collagenase shown in FIGS. 2 and 5. The histidine residue is required for binding competition.

FIG. 7 illustrates a time course for pAPMA activation Of type IV procollagenase followed by gelatin zymogram and western blotting. 20 μl aliquots of A2058 melanoma cell conditioned media were activated in the presence of 1.0 mM pAPMA for the indicated times (min). The reactions were stopped by the addition of EDTA to 10 mM and the samples were electrophoresed on a 9% acrylamide gel with or without gelatin. The gelatin containing gels were developed as zymograms after electrophoresis. The nongelatin containing gels were electrophoretically transferred to nitrocellulose and then immunostained with the designated affinity purified antibodies (1 μg/ml). Loss of the amino terminal antigenic domain occurs during the pAPMA induced conversion from the 70 kDa to the 62 kDa form. MWM, prestained molecular weight markers.

Figure 8:
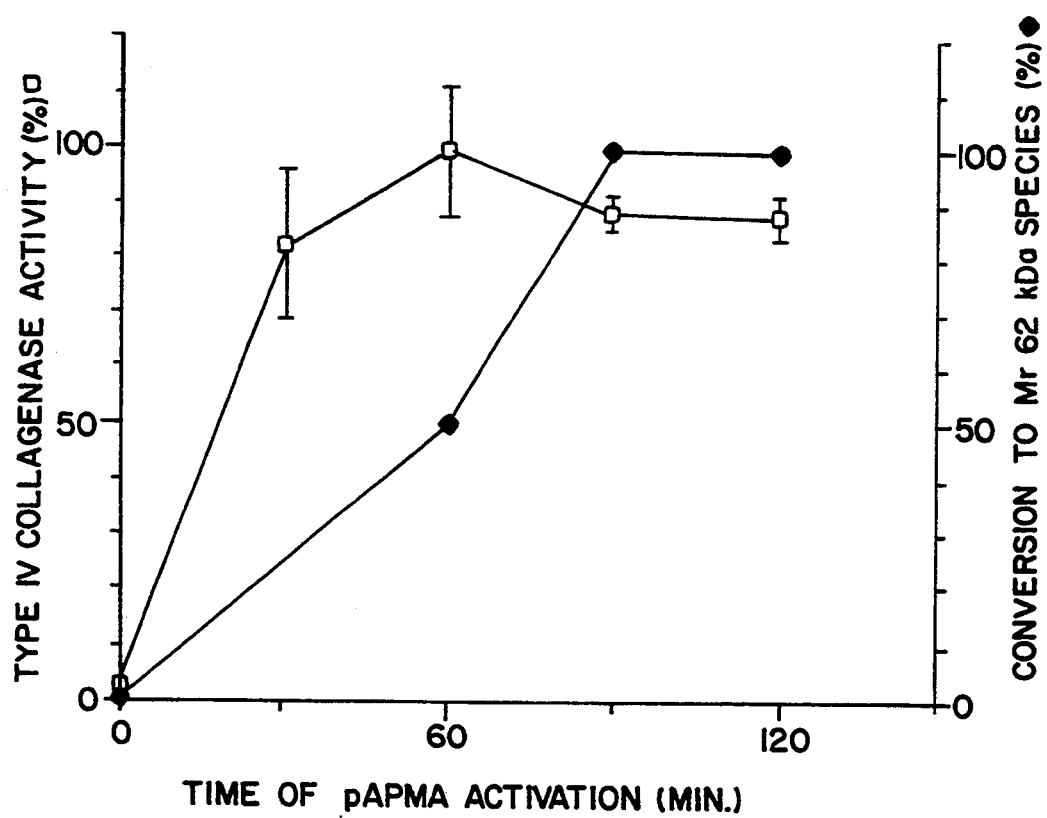

FIG. 8 illustrates a time course of pAPMA activation of purified type IV collagenase followed by type IV collagen degradation assay. 10 μl aliquots of purified type IV collagenase (23 μg/ml) were made 1 mM in pAPMA and preincubated at 37° C. for the indicated times. The samples were then diluted to 60 μl final volume by the addition of 50 mM Tris HCl, 0.15M NaCl, 5 mM $CaCl_2$, pH 7.6 $^3$H-type IV collagen (New England Nuclear) was added and the reaction mix allowed to incubate at 37° C. for 30 min. Samples were assayed in triplicate. Maximal activity corresponds to 2.8 μg type IV collagen degraded/h/μg purified enzyme at 37° C.

Figure 9:
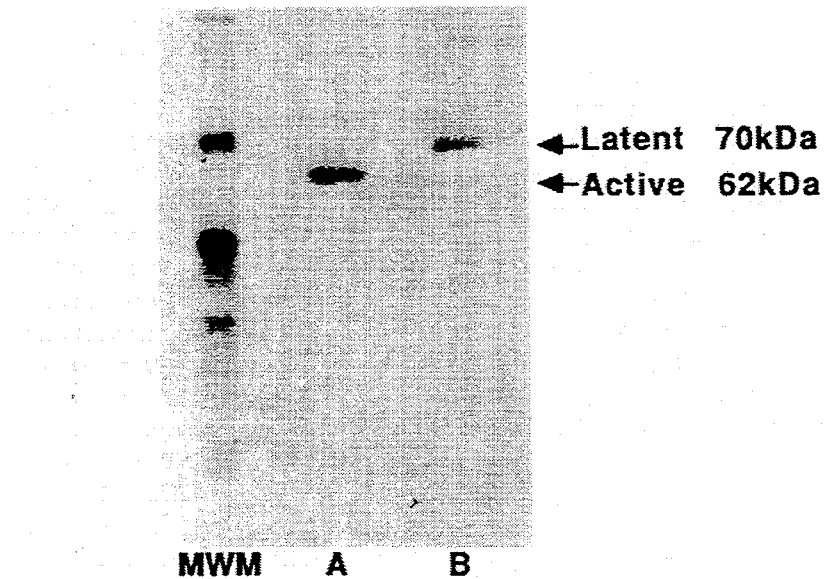

FIG. 9 illustrates the amino acid sequences of the latent and active forms of type IV procollagenase as determined by direct amino acid sequencing of the purified enzyme. Also shown is the cleavage site of the autocatalysis on pAPMA activation. The insert shows the apparent molecular weights on a silver stained $NaDodSO_4$-PAGE gel of the purified latent (20 ng, lane A) and active enzymes (20 ng, lane B).

FIG. 10 illustrates the amino termini (residues 1–110) of type IV procollagenase (top line), interstitial procollagenase (middle line), and prostromelysin (bottom line). The area of homology just upstream from the cleavage site is shown in box A, the cleavage sites following pAPMA activation are shown in box B and the cysteine residues are underlined. Additional reported sites of cleavage following pAPMA treatment of interstitial collagenase and stromelysin are denoted by asterisks.

Figure 11:
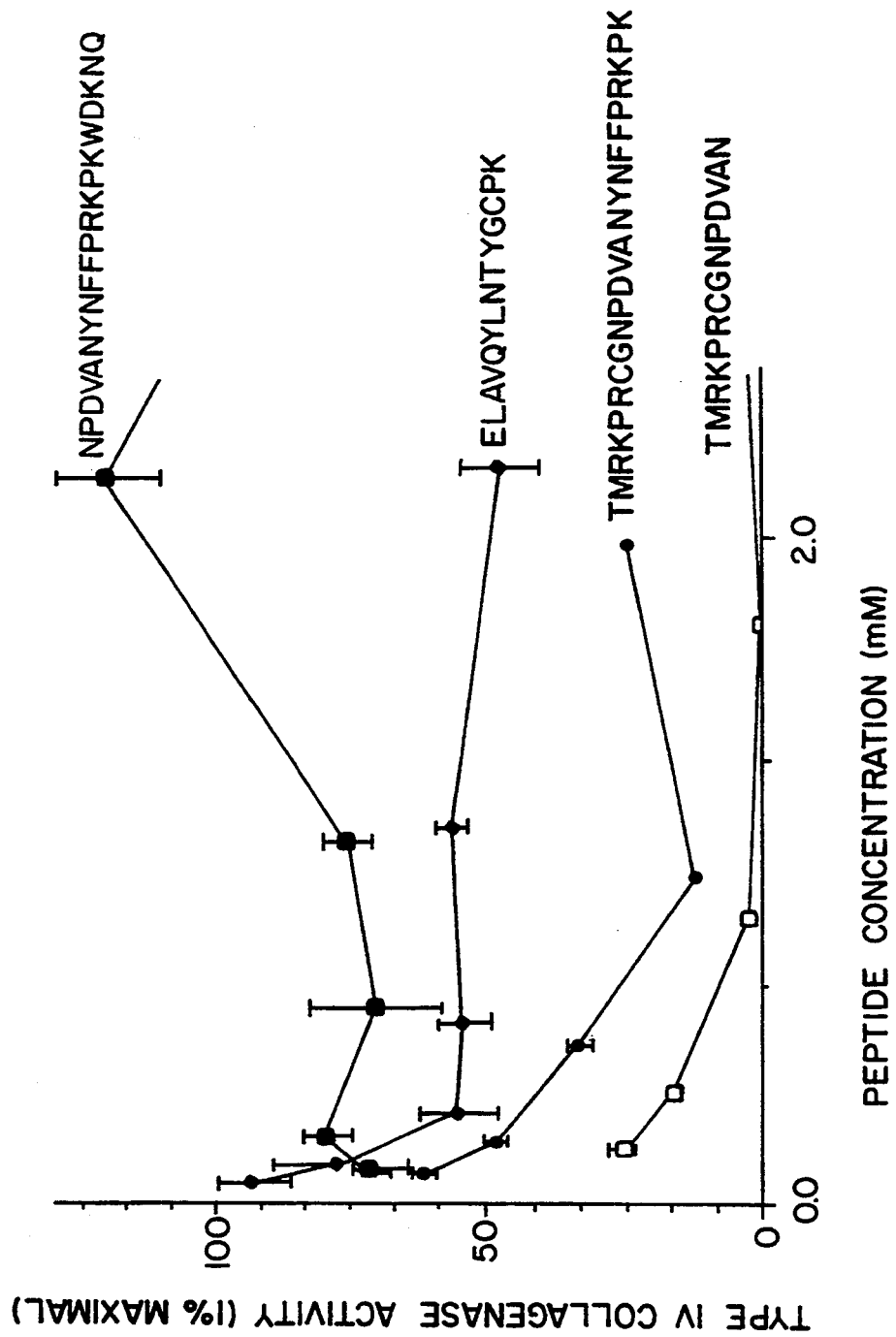

FIG. 11 illustrates the dose dependent inhibition of purified activated type IV collagenase cleavage of pepsinized type IV collagen by the designated synthetic peptides. Peptide TMRKPRCGNPDVAN at a concentration of 0.1 mM inhibits 80% of the enzyme activity. Higher concentrations abolish all enzyme activity.

FIG. 12 illustrates a comparison of peptides tested for enzyme inhibitory activity. The peptides were derived from the amino terminal sequence shown in FIG. 10. The core sequence PRCG is necessary for inhibitory activity based on the fact that peptides lacking this sequence are devoid of significant inhibitory activity. Further refinement of the minimal sequence requirements was accomplished using the peptides listed in Table 2.

FIG. 13 illustrates the nucleotide sequence of the portion of a human cDNA clone for human type IV procollagenase which encodes the 80 amino acid sequence of the amino terminal peptide that is cleaved from human type IV procollagenase upon activation.

DETAILED DESCRIPTION OF THE INVENTION

It is the object of this invention to provide peptide sequences that have the ability to inhibit a matrix metalloproteinase.

It is a further object of the invention to provide antibodies for use in identifying the presence of a matrix metalloproteinase.

It is a further object of this invention to provide a method of treating patients suffering tissue damage arising from tissue destruction caused by an activated matrix metalloproteinase.

Figure 1:
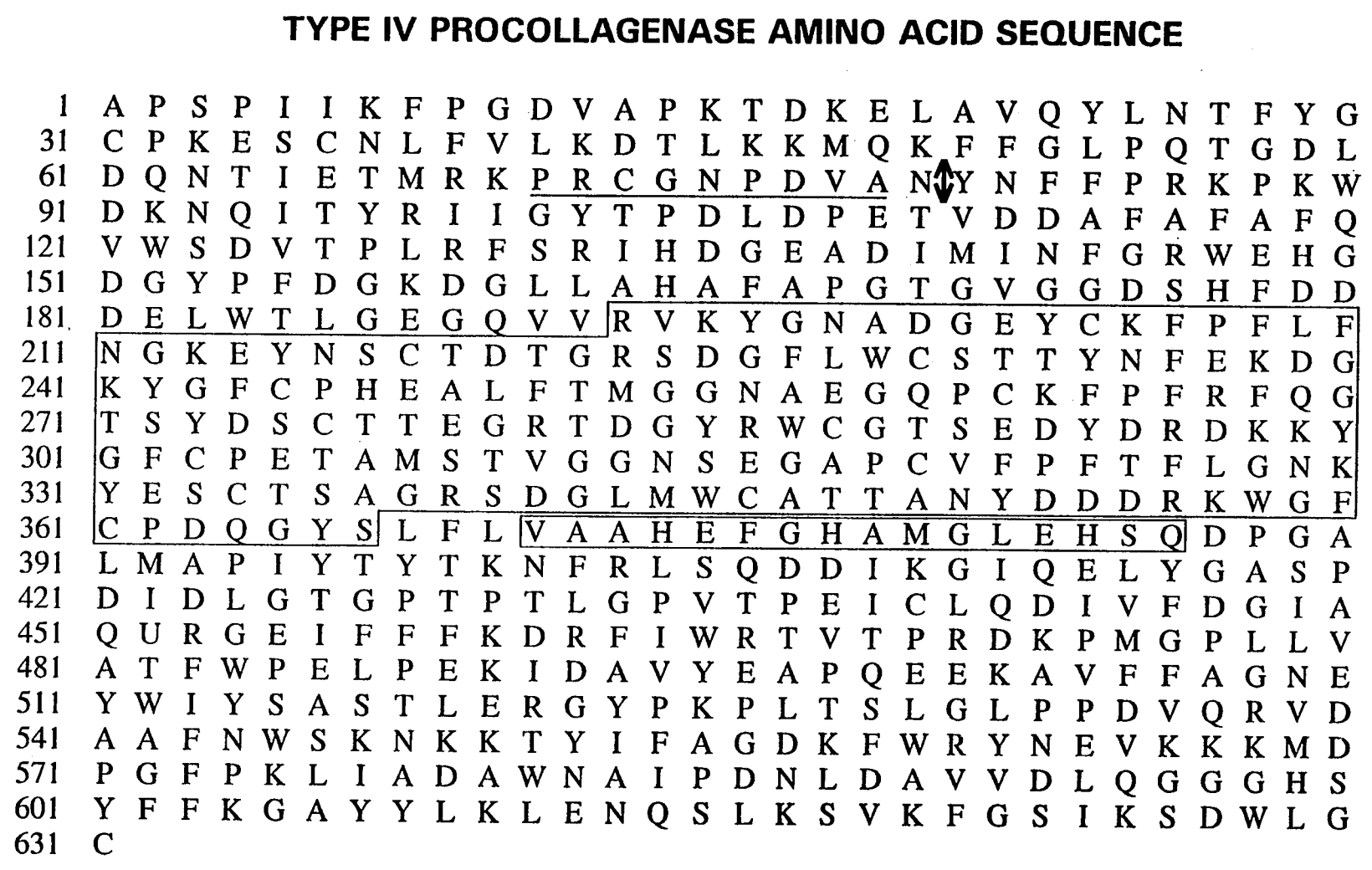
Figure 2:
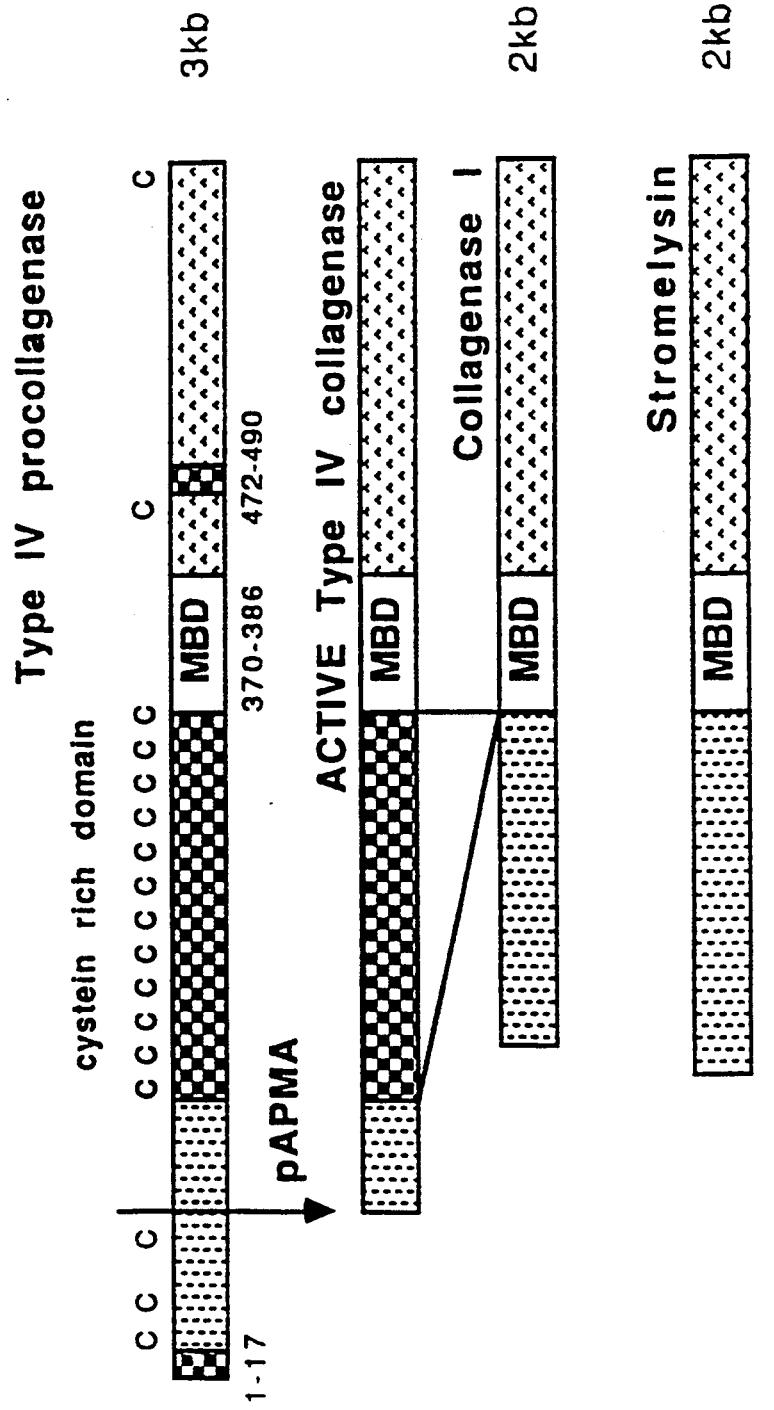
FIG. 2 illustrates a comparison of amino acid homologies between type IV procollagenase and prostromelysin and procollagenase I organized into domains.

The complete amino acid sequence of the human type IV collagenase is illustrated in FIG. 1. This sequence reveals that this protein can be divided into a series of domains as shown in FIG. 2. A cysteine-rich (12 cysteine residues) domain encoded by a segment of approximately 1 kb has no significant homology with other sequenced metalloproteinases such as type I collagenase and stromelysin. The cysteine-rich region, however, does show significant homology to fibronectin. The cysteine-rich sequence has never previously been directly tested for its functional role in the metalloproteinase activity. Peptides derived from the cysteine-rich region (residues 200–370) inhibited enzyme substrate binding and are considered embodiments of the present invention.

Three other domains of type IV collagenase show significant homologies with other matrix metalloproteinases (FIG. 2). In particular, a region at residues 371 to 386, designated "MBD" and illustrated in FIG. 2, has closely homologous sequences in all three matrix metalloproteinases including thermolysin. In the actual crystallized thermolysin, this region is related to the putative Zn binding domain of the enzyme. However, the MBD sequence has never previously been directly tested for its functional role in the metalloproteinase activity. In the present invention (a) synthetic peptides derived from these regions, and (b) affinity purified antibodies directed against these regions constitute inhibitors which block gelatinase and type IV collagenase activity. Furthermore, peptides derived from fibronectin homologous to the type IV collagenase domains outlined also inhibit binding of type IV collagenase to its substrates.

The matrix metalloproteinase inhibitors of this invention can be used in the treatment of inappropriate angiogenesis, arthritis, tumor growth, invasion and metastasis, and granulomatous inflammatory conditions such as sarcoidosis. In these conditions, it is possible to estimate the amount of enzyme produced and the amount of peptide inhibitor required to inhibit greater than 90% of the active enzyme as shown in FIG. 11. Therapeutic dose of the inhibitory peptide falls within an acceptable pharmacologic range of 10–250 mg/kg/d, with a more preferred dosage being 25–100 mg/kg/d. The dosage for a given patient will depend on the amount of enzyme produced in the patient, the condition and size of the patient. The inhibitors may be given as infusions or by any means which provides ready transmission into the circulation. Lyophilized powders may be "snorted". Preparations for buccal or sublingual administration may also be given. For respiratory tract involvement, the peptides may be administered by inhalation. Aerosols are particularly useful for this purpose. For conditions of the eye, the peptides may be administered as eye drops.

EXAMPLE 1

Histidine Containing Peptide Inhibitors

The synthetic peptide corresponding to residues 371–386 (the MBD region) of type IV collagenase abolished the gelatinase and the collagenase type IV activity. This is demonstrated in FIG. 5 using gelatin zymograms. Furthermore, affinity purified antibodies recognizing these domains also inhibited the gelatinase and collagenase type IV activities. The mechanism of action of these peptides was, at least in part, due to their ability to complete for binding of type IV collagenase to type IV collagen (FIG. 6).

The metalloproteinase peptide inhibitor has a protein peptide having substantial homology with a histidine-containing domain at residues 371 to 386 of type IV collagenase. The protein peptide inhibits gelatinolytic and collagenolytic activities of metalloproteinases. The protein peptide of the metalloproteinase inhibitor preferably contains at least one histidine residue for activity. One desirable embodiment of the protein peptide of the metalloproteinase inhibitor has a histidine-containing sequence, said sequence being a member selected from the group consisting of VAAHEFGHAMGLEHSQ, VAAEFGAAMGLEHSQ, VAAHELGHSLGLSHST, VAAHELGHSLGLSHST, VAAHEIGHSLGLFHSA, VVAHELTHAVTDYTAG and the fibronectin peptide AAHEEICTTNEGVM. Since the latter peptide was effective and required the histidine residue, the core sequence AHE was determined to be a minimum determinant of one major embodiment of the invention.

By substituting amino acids into conserved residue regions, it was demonstrated that the histidine residues were, in part, required for the inhibitory activity of the peptide as shown in FIGS. 5 and 6. When all three histidines were replaced with alanines, the peptide was completely inactive. However, if only the central histidine was replaced by alanine, the inhibitory activity was retained. Furthermore, replacement of the two glutamic acid (E) residues with glutamine (Q) substantially altered the inhibitory activity of the peptide. These inhibitory peptides bear no homology to the cleavage site on the type IV collagen or gelatin substrate. Their mechanism of action involves an interference of the enzyme-substrate interaction in a region of the proteinase which can interact with a metal ion, such interaction being necessary for substrate cleavage. The active peptide partially inhibited the gelatinolytic activity of thermolysin under concentrations of the peptide which abolished the type IV collagenase activity. The active peptides failed to inhibit a variety of serine and thiol proteases or "non-metalloproteinases" tested, including plasmin and trypsin.

TABLE 1 is a list of the synthetic histidine-containing peptides, including amino acid substitutions, that have been tested as candidates for inhibitors of a matrix metalloproteinase, chosen from the sequence in FIG. 1, based on functional studies by the inventors and based on homology comparisons with other metalloproteinases.

TABLE 1

Synthetic Histidine-Containing Peptides Tested for Inhibition of Type-IV Collagenase (N->C)

1. Val-Ala-Ala-His-Glu-Phe-Gly-His-Ala-Met-Gly-Leu-Glu-His-Ser-Gln
2. Val-Ala-Ala-Ala-Glu-Phe-Gly-Ala-Ala-Met-Gly-Leu-Glu-Ala-Ser-Gln
3. Val-Ala-Ala-His-Gln-Phe-Gly-His-Ala-Met-Gly-Leu-Gln-His-Ser-Gln
4. Val-Ala-Ala-His-Glu-Phe-Gly-Ala-Ala-Met-Gly-Leu-Glu-His-Ser-Gln
5. Val-Ala-Ala-Ala-Glu-Phe-Gly-His-Ala-Met-Gly-Leu-Glu-His-Ser-Gln
6. Val-Ala-Ala-Ala-Glu-Phe-Gly-Ala-Ala-Met-Gly-Leu-Glu-His-Ser-Gln
7. Val-Ala-Ala-His-Glu-Phe-Gly-Ala-Met-Gly-Leu-Glu-Ala-Ser-Gln
8. Val-Ala-Ala-His-Ala-Phe-Gly-His-Ala-Gly-Leu-Ala-His-Ser-Gln
9. Val-Val-Ala-His-Glu-Leu-Thr-His-Ala-Val-Thr-Asp-Tyr-Thr-Ala-Gly
10. Val-Ala-Ala-Glu-Lys-Phe-Gly-Glu-Ala-Met-Gly-Leu-Lys-Glu-Ser-Gln
11. Ala-Ala-His-Glu
12. Ala-Ala-His-Glu-Glu-Ile-Cys-Thr-Thr-Asn-Glu-Gly-Val-Met
13. Ala-Ala-Ala-Glu-Glu-Ile-Cys-Thr-Thr-Asn-Glu-Gly-Val-Met
14. Thr-Met-Arg-Lys-Pro-Arg-Cys-Gly-Asn-Pro-Asp-Val-Ala-Asn-Tyr-Asn-Phe-Phe-Pro-Arg-Lys-Pro-Lys
15. Thr-Met-Arg-Lys-Pro-Arg-Cys-Gly-Asn-Pro-Asp-Val-Ala-Asn
16. Thr-Met-Arg-Lys-Pro-Arg-Ser-Gly-Asn-Pro-Asp-Val-Ala-Asn
17. Arg-Lys-Pro-Arg-Cys-Gly-Asn
18. Glu-Ser-Cys-Asn-Leu-Phe-Val-Leu-Lys-Asp-Thr-Leu-Lys-Met-Gln-Lys
19. Met-Trp-Cys-Ala-Thr-Thr-Ala-Asn-Tyr-Asp-Asp-Arg-Lys-Trp-Gly-Phe-Cys-Pro-Asp-Gln-Gly-Tyr-Ser-Leu

Methods

Gelatin Zymogram

A gelatin zymogram for visualization gelatinase activity was prepared using the stock solutions and mixing procedures below.

| Stock Solutions: | Mixing Procedures: |
|---|---|
| a) 2M Tris HCl, pH 8.8 | 242 g Tris base in 800 ml of dH$_2$O, adjust pH to 8.8 with concentrated HCl |

| Stock Solutions: | Mixing Procedures: |
|---|---|
| | and dilute to 1 liter |
| b) 0.5M Tris pH 6.8 | 6.05 g Tris base in 80 ml of dH$_2$O, adjust pH to 6.8 with concentrated HCl and dilute to 100 ml |
| c) 30% Acrylamide with 0.8% bisacrylamide, | To 100 g of acrylamide, add 2.4 g of bisacrylamide, add enough dH$_2$O to dissolve acrylamide. Dilute to 333 ml and store at 4° C. in an aluminum foil wrapped bottle |
| d) 10% SDS | Dissolve 100 g of SDS in dH$_2$O and dilute to 1 liter final volume |
| e) 10% Ammonium persulfate | To 1 g of ammonium persulfate, add dH$_2$O to 10 ml final volume. Store at 4° C. |
| f) 10 × Electrode buffer | Dissolve 144 g glycine in 600 ml of dH$_2$O add 125 ml of 2M Tris HCl, pH 8.8, and 100 ml of 10% SDS. Dilute to final volume of 1 liter |
| g) 5 × Sample buffer | Dissolve 50 mg bromophenol blue in 2.5 ml of 0.5M Tris HCl, pH 6.8, add 4 ml 10% SDS, 2.5 ml of glycerol and store at 4° C. |
| h) TEMED | |
| i) 1% Gelatin | Dissolve 1 g of gelatin in 100 ml of dH$_2$O by warming suspension under running hot tap water |
| j) Gel staining solution | 30% methanol, 10% acetic acid, 0.1% amido black 10 |
| B | |
| k) Destaining solution | 30% methanol, 10% acetic acid |

Procedure

The procedure for preparing the gelatin zymogram used for this example utilized the following steps and reagents.

1) Assemble gel forming apparatus.
2) Prepare resolving gel solution for polymerization: 9% acrylamide 40 ml final volume: in a 50 ml falcon tube 12 ml 30% acrylamide, 0.8% bisacrylamide 0.4 ml 10% SDS 7.5 ml 2M Tris HCl, pH 8.8 4 ml 1% gelatin 16 ml dH20
3) After mixing, add 0.4 ml 10% ammonium persulfate and mix again.
4) Initiate polymerization with 40 µl of TEMED, mix and pour 32 ml of gel solution into the gel form.
5) Overlay solution with water saturated butanol and allow 30–45 minutes to polymerize.
6) After polymerization, wash gel surface with dH$_2$O and allow to dry.
7) Prepare stacking gel solution for polymerization: 3% acrylamide 10 ml final volume: to a 15 ml falcon tube add 2.5 ml 0.5M Tris HCl, pH 6.8 0.1 ml 10% SDS 1.0 ml 30% acrylamide, 0.8% bisacrylamide 0.1 ml 10% ammonium persulfate 5.3 ml dH$_2$O
8) Initiate polymerization of stacking gel with 40 µl TEMED and mix.
9) Pour approximately 6 ml into gel form over polymerized running gel and insert well comb.
10) Remove air bubbles from the bottom of the comb teeth and add additional gel solution, if needed.
11) Allow stacking gel to polymerize 15–20 min.
12) After polymerization, remove comb from stacking gel and add 1 X electrode buffer to both electrode chambers.
13) Remove air bubbles from sample wells and bottom of gel.
14) Load samples and run electrophoresis at 30 mamps/gel.
15) After completion of electrophoresis, wash gel in two changes of 2.5% Triton X-100 for 60 minutes with gentle agitation at room temperature.
16) Discard Triton X-100 solution and place gel in 1 X collagenase buffer, incubate at 37° C. for 2–4 hours or overnight at room temperature.
17) After incubation period, stain gel for 30 minutes in 0.1% amido black and then destain for approximately 90 minutes.
18) Zones of clearing correspond to gelatinolytic activity.

The preparation of separating gels of various concentrations are shown below.

| | 40 ml final volume | | | |
|---|---|---|---|---|
| | 6% | 8% | 9% | 10% |
| 30% acrylamide, 0.8% bis | 8 ml | 10.6 ml | 12 ml | 13.3 ml |
| dH$_2$O | 20 ml | 17.4 ml | 16 ml | 14.7 ml |

Soluble Collagenase Assay

The procedure for the collagenase assay of this example utilized the following preparation.

A 10 X collagenase buffer was prepared to obtain final concentrations of 0.5M Tris, 2.0M NaCl, 0.05M CaCl$_2$, 2% Brij 35. To prepare one liter, combine:
60.55 g Tris
116.88 g NaCl
7.35 g CaCl$_2$
20 g Brij 35
Then dissolve in 800 ml of dH$_2$O and adjust the pH to 7.6 with the addition of concentrated HCl. Adjust the final volume to 1 liter and filter sterilize.

A 10 X bacterial collagenase (positive control) was prepared to obtain a final concentration of 0.5% (w/v). This involved the dissolving of 10 mg of bacterial collagenase (Sigma #C-5138) in 2 ml of 1 X collagenase buffer and storing at −20° C. in 100 ml aliquots.

A bovine serum albumin (carrier protein) solution was prepared to obtain a final concentration of 0.5% (w/v) bovine serum albumin in 1 X collagenase buffer. This involved the dissolving of 100 mg of bovine serum albumin in 20 ml of 1 X collagenase buffer and storing aliquoted in 1 ml fractions at −20° C.

A trichloroacetic acid-tannic acid-proline solution (TCATAP) was prepared to obtain a final concentration of 10% TCA, 0.5% tannic acid, 2 mM proline. This involved the combining of 10 ml of 100% trichloroacetic acid solution, 10 ml of 5% tannic acid solution and 1 ml of 200 mM proline solution, diluting to 100 ml final volume and store at 4° C., and replacing this solution every 4 weeks.

Procedure

1. Place enzyme sample activator (usually 1 mM pAPMA) and test solution in 1.5 ml Eppendorf tube. Combined volume must equal 60 µl. Add 1 X collagenase buffer, if necessary. If necessary, preincubate.
2. Prepare type IV collagen substrate by diluting stock $^3$H-type IV collagen (NEN #NET-931 lot

2511-018) 1:120 with 1 X collagenase buffer. Heat to 55° C. for 10 minutes and cool on ice.

3. Add 5 μl of diluted ³H-type IV collagen solution to each assay tube. Vortex to mix and incubate at 28° C. for 4 hours.
4. At the end of the incubation period, add 2 μl of carrier BSA solution and 7 μl of TCATAP solution. Vortex mix and allow to stand on ice for at least 10 minutes.
5. Pellet the precipitate by centrifuging in the microfuge for 10 minutes with the speed set at 6. Orient the tubes when placing them in the microfuge in order that the position of the pellet will be known.
6. Immediately after centrifugation, aspirate 55 μl of the supernatant and place in a scintillation vial. Add 5 ml of scintillation cocktail, shake well and count.

EXAMPLE 2

Cysteine Containing Peptide Inhibitors

The amino terminal sequence of A2058 melanoma cell type IV procollagenase (residues 1–17, AP-SIIKFPGDVAPKTD) as well as that of an internal domain (residues 472–490, DKPMGPLLVATFW-PELPEK) were synthesized for use in preparation of monospecific antibodies. These peptides were chosen because they were obtained in the direct sequencing of the enzyme (Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, *J. Biol. Chem* 263, 6579–6587; Hoyhtya, M., Turpeenniemi-Hujanen, T., Stetler-Stevenson, W., Krutzsch, H., Tryggvason, K., and Liotta, L. A., 1988, *FEBS Letters* 233, 109–113), were confirmed in the predicted sequence from the cDNA clone (Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, *J. Biol. Chem* 263, 6579–6587), and are derived from regions which do not show homology with the other metalloproteinases. The affinity purified antibodies were characterized using direct ELISA as well as competition experiments. The antibodies showed no cross reactivity with bovine serum albumin or unrelated peptides. The affinity purified antibodies are capable of immunoprecipitating the type IV procollagenase (Hoyhtya, M., Turpeenniemi-Hujanen, T., Stetler-Stevenson, W., Krutzsch, H., Tryggvason, K., and Liotta, L. A., 1988, *FEBS Letters* 233, 109–113). Western blots demonstrated that both antibodies recognized the type IV procollagenase as a single band in A2058 conditioned media identical to the Western blotting with the purified type IV collagenase.

The time course for pAPMA activation was followed using gelatin zymogram analysis, type IV collagenase assays and both affinity purified antibodies on immunoblots (FIG. 7). Gelatin zymogram (FIG. 7) analysis of A2058 melanoma cell type IV collagenase revealed a single band of gelatinolytic activity with a molecular weight of 70 kDa daltons. Incubation at 37° C. in the presence of 1 mM pAPMA resulted in,gradual conversion of this band of gelatinolytic activity to a lower molecular mass of 62 kDa. This conversion was completely inhibited in the presence of 10 mM EDTA and did not occur in the absence of added pAPMA (not shown). Type IV collagenase assays of the purified type IV procollagenase revealed no collagenolytic activity in the absence of the organomercurial compound pAPMA during the incubation period. The enzyme could be activated by preincubation with pAPMA. The time course of activation during preincubation with pAPMA as measured by collagenase assay shows that full collagenolytic activity is obtained rapidly (FIG. 8). Antibody A472-490 demonstrated a time dependent reduction in molecular weight with incubation that corresponds to that seen in the gelatin zymograms (FIG. 7). This conversion appeared 50% complete by the 60 minute time point and essentially complete by the 90 minute. Antibody A1-17 corresponding to the amino terminal epitope showed a direct reduction in immunostaining during the course of pAPMA activation. These results indicate that the apparent molecular weight reduction following conversion of the latent to a stable, active collagenase with the organomercurial compound is the result of the loss of an amino terminal peptide fragment.

Figure 3D:
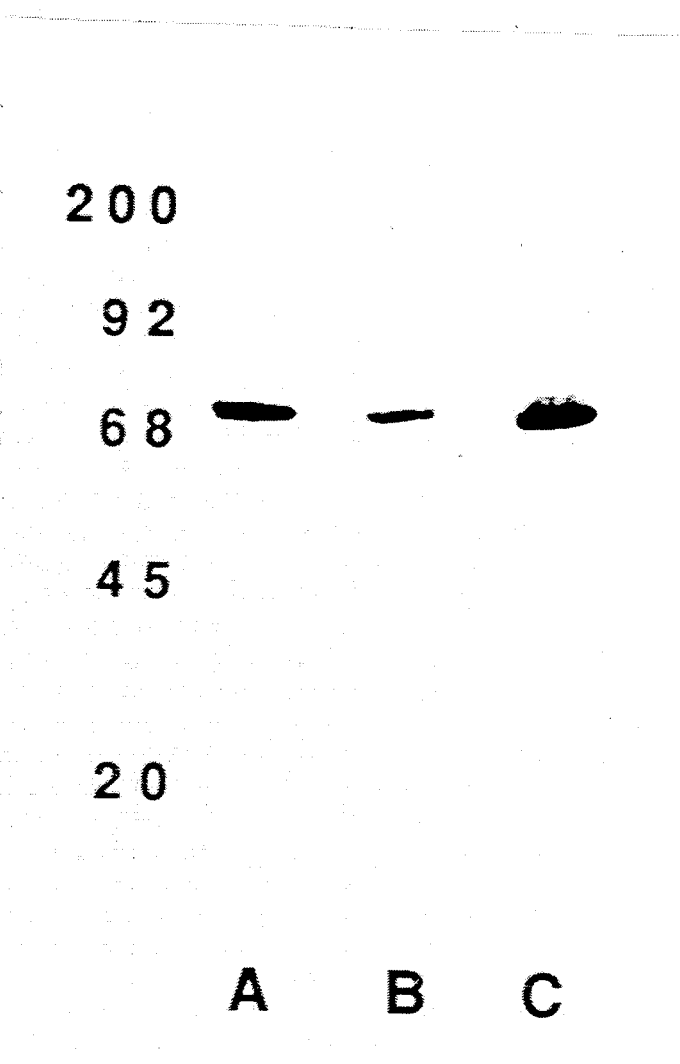

Gelatin-affinity purified type IV procollagenase was further purified by reverse phase HPLC both before and after pAPMA activation. The chromatograms showed essentially no change in the retention times for the latent and active forms. When the peaks were collected and analyzed by NaDodSO₄-PAGE, the procollagenase peak prior to pAPMA activation showed a single band at approximately 70 kDa under non-reducing conditions (FIG. 9, insert). The collagenase peak after pAPMA activation (16 hours, 37° C.) showed a single band at 62 kDa under non-reducing conditions (FIG. 3A).

The material obtained from the procollagenase peak on HPLC prior to pAPMA activation was subjected to direct amino acid sequencing. This material gave an amino terminal sequence that was identical to that previously determined for this enzyme (FIG. 9). Direct sequencing of the pAPMA activated material, after HPLC purification, revealed a single new amino terminal sequence (FIG. 9). This definitively demonstrates that pAPMA activation is accompanied by an autocatalytic removal of an amino terminal peptide fragment from the latent enzyme with a reduction in the molecular mass of about 8 kD. This cleavage occurs at only a single site as no evidence of any other amino terminal amino acids were detected upon sequencing many preparations of the purified, activated enzyme and no evidence of intermediates were detected by Western blotting or gelatin zymogram analysis.

The results of this study demonstrates that type IV collagenase is secreted in a latent proenzyme form requiring activation before obtaining collagenolytic activity. The organomercurial compound pAPMA is capable of this activation. Organomercurial activation of type IV procollagenase is accompanied by conversion of the proenzyme form to a lower molecular weight, active enzyme form by removal of an 80 amino acid residue peptide fragment from the amino terminus. Maximum collagenolytic activity is obtained rapidly following exposure to pAPMA. The attainment of this activity prior to complete conversion to the stable lower molecular weight form is consistent with a conformational rearrangement in the zymogen form that results in an active but unstable species, as has been reported for interstitial collagenase and stromelysin (Stricklin, G. P., Jeffrey, J. J., Roswit, W. T., and Eisen, A. Z., 1983, *Biochemistry* 22, 61–68; Murphy, G., Cockett, M. I., Stephens, P. E., Smith, B. J., and Docherty, A. J. P., 1987, *Biochem. J.* 248, 265–268). Activation occurs with highly purified type IV procollagenase enzyme. Thus, the activation in the presence of the organomercurial compound is autoproteolytic since pAPMA is itself incapable of peptide bond hydrolysis. This autocatalytic mechanism of activation with organomercurial compounds has been demonstrated for other extracellular matrix degrading metalloproteinases, such as interstitial collagenase (Grant, G. A., Eisen, A. Z., Marmer, B. L., Rosweit, W. T., and Goldberg, G. I., 1987, J. Biol. Chem. 262, 5886-5889; Whitman, S. E., Murphy, G., Angel, P., Rahmsforf, H. -J., Smith, B. J., Lyons, A., Harris, T. J. T., Reynolds. J. J., Herrlich, P. and Docherty, A. J. P., 1986, Biochem. J. 240, 913-916), and stromelysin (Wilhelm, S. M., Collierm, I. E., Kronberger, A., Eisen, A. Z., Marmer, B. L., Grant, G. A., Bauer, E., and Goldberg, G. I., 1987, Proc. Natl. Acad. Sci. U.S.A. 84, 6725-6729; Whitman, S. E., Murphy, G., Angel, P., Rahmsforf, H. -J., Smith, B. J., Lyons, A., Harris, T. J. T., Reynolds. J. J., Herrlich, P. and Docherty, A. J. P., 1986, Biochem. J. 240, 913-916; Murphy, G., Cockett, M. I., Stephens, P. E., Smith, B. J., and Docherty, A. J. P., 1987, Biochem. J. 248, 265-268; Sanchez-Lopez, R., Nicholson, R., Gensel, M. C., Matrisian, L., and Breatnach, R., 1988, J. Breathnach, R., 1988, J. Biol. Chem. 263, 11892-11899). These three metalloproteinase, type IV procollagenase, interstitial procollagenase and prostromelysin show significant homology at the amino acid level (Grant, G. A., Eisen, A. Z., Marmer, B. L., Rosweit, W. T., and Goldberg, G. I., 1987, J. Biol. Chem. 262, 5886-5889; Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, J. Biol. Chem 263, 6579-6587; Wilhelm, S. M., Collierm, I. E., Kronberger, A., Eisen, A. Z., Marmer, B. L., Grant, G. A., Bauer, E., and Goldberg, G. I., 1987, Proc. Natl. Acad. Sci. U.S.A. 84, 6725-6729; Saua, J., Quinones, S., Otani, Y., Nagase, H., Harris, E. D., Jr., and Kurkinen, M., 1988, J. Biol. Chem. 263, 6742-6745; Whitman, S. E., Murphy, G., Angel, P., Rahmsforf, H. -J., Smith, B. J., Lyons, A., Harris, T. J. T., Reynolds. J. J., Herrlich, P. and Docherty, A. J. P., 1986, Biochem. J. 240, 913-916; Sanchez-Lopez, R., Nicholson, R., Gensel, M. C., Matrisian, L., and Breatnach, R., 1988, J. Breathnach, R., 1988, J. Biol. Chem. 263, 11892-11899).

When the amino acid sequences for the amino termini of these enzymes are aligned for maximum homology (FIG. 10), two correlations are observed. First, the site of autoproteolysis in type IV collagenase upon activation with pAPMA, which result in a stable, active enzyme, occurs at an identical locus to that previously reported for prostromelysin activation and the major product of interstitial procollagenase activation (Whitman, S. E., Murphy, G., Angel, P., Rahmsforf, H. -J., Smith, B. J., Lyons, A., Harris, T. J. T., Reynolds. J. J., Herrlich, P. and Docherty, A. J. P., 1986, Biochem. J. 240, 913-916; Murphy, G., Cockett, M. I., Stephens, P. E., Smith, B. J., and Docherty, A. J. P., 1987, Biochem. J. 248, 265-268). Similar sites of autoproteolysis following pAPMA treatment have been reported by others for prostromelysin (Wilhelm, S. M., Collierm, I. E., Kronberger, A., Eisen, A. Z., Marmer, B. L., Grant, G. A., Bauer, E., and Goldberg, G. I., 1987, Proc. Natl. Acad. Sci. U.S.A. 84, 6725-6729) and interstitial procollagenase (Grant, G. A., Eisen, A. Z., Marmer, B. L., Rosweit, W. T., and Goldberg, G. I., 1987, J. Biol. Chem. 262, 5886-5889). Second, the amino terminal peptide fragments which are removed during activation of all three enzymes contain an odd number of cysteine residues. In type IV procollagenase, three cysteine residues are present in the removed peptide fragment; Cys-31, Cys-36 and Cys-73. In interstitial procollagenase and prostromelysin, there is a single cysteine residue present in the removed peptide fragment that corresponds to Cys-73 in type IV procollagenase. Thus, the conversion from an odd number of cysteine residues in the latent metalloproteinase to an even number of cysteine residues in the pAPMA activated form, appears to be a common feature in all three enzymes. The removal of an unpaired cysteine may be of functional significance. Finally, all three enzymes contain a highly conserved region immediately upstream to the activation locus consisting of the amino acid sequence PRCGVPDV. This sequence contains the unpaired cysteine residue in the propeptides of interstitial collagenase and stromelysin (Whitman, S. E., Murphy, G., Angel, P., Rahmsforf, H.-J., Smith, B. J., Lyons, A., Harris, T. J. T., Reynolds. J. J., Herrlich, P. and Docherty, A. J. P., 1986, Biochem. J. 240, 913-916) and by homology the unpaired cysteine (out of the three present) in the type IV collagenase propeptide. A recent report has shown by site-directed mutagenesis studies of rat transin (homolog of human stromelysin), the importance of this conserved region in the autoactivation of this family of metalloproteinases. Recombinant transin forms containing mutations in this sequence showed a higher rate of spontaneous activation when compared with the native sequence (Sanchez-Lopez, R., Nicholson, R., Gensel, M. C., Matrisian, L., and Breatnach, R., 1988, J. Breathnach, R., 1988, J. Biol. Chem. 263, 11892-11899).

Therefore, the present inventors have used the gelatin zymogram technique to test a number of small peptides related to the type IV procollagenase activation locus for their ability to inhibit type IV collagenase enzyme activity. As shown in FIGS. 11 and 12, only those peptides incorporating the conserved region (PRCGVPDV) containing the unpaired cysteine were strongly inhibitory at concentration less than 0.1 nM. The cysteine was required for the activity. Table 2 shows that the minimal peptide sequence which retained inhibitor activity was actually the pentapeptide sequence RKPRC.

TABLE 2

Minimal Peptide Sequence and Sequence Requirements for Inhibition of Type IV Collagenase.

| Peptide # | Sequence | Inhibition[a] |
|---|---|---|
| 74 | TMRKPRCGNPDVAN | + |
| 78 | TMRKPRSGNPDVAN | − |
| 82 | KPRCG | − |
| 85 | MRKPRCG | + |
| 86 | KPRCGNP | − |
| 88 | RKPRC | + |
| 93 | RQPRC | + |
| 94 | RKARC | + |
| 95 | QKPRC | − |
| 101 | RKPQC | − |
| 106 | KKPRC | + |
| 107 | RKPKC | + |
| 108 | RKLRC | + |

[a]Inhibitory activity was assessed using the modification of the gelatin zymogram technique described for Example 1. All peptides were tested at a final concentration of 1 mg/mL.

The data in Table 2 further demonstrate that peptide inhibitor activity requires specific charged sequence elements flanking a critical cysteinyl residue. Specifically, the two arginyl residues of the conserved sequence appeared critical for inhibitory activity. Substitution with polar uncharged residues at these positions (R to Q) resulted in loss Of activity. However, the prolyl and lysyl residues between these two arginyl residues could be replaced with glycyl residues and these peptides retained inhibitory activity. This suggests that the lysyl and prolyl residues which may be important for the local conformation of this region (Sanchez-Lopez et al., 1988), do not appear to directly participate in the inhibitory interaction.

Thus the proenzyme fragment of type IV collagenase contains a conserved sequence which is shared with other members of the matrix metalloproteinase family. This sequence is capable of inhibiting the activated type IV collagenase. This inhibitor sequence requires the presence of an unpaired cysteinyl residue within a specific flanking peptide sequence that contains two positively charged residues at positions −1 and −4 with respect to the essential cysteinyl residue. Inhibition of enzyme action by this inhibitor appears to be specific in that it requires two elements for inhibitor activity, an unpaired cysteinyl residue within a defined peptide sequence.

These data support the novel hypothesis that the RKPRC sequence which is present in the proenzyme fragment acts as an endogenous inhibitor of the enzyme through interaction of the cysteinyl residue with the metal atom coordinated at the active site. Furthermore, the sequence that surrounds the unpaired cysteinyl residue appears to promote this inhibitory interaction as amino acid substitutions at positions adjacent to the cysteinyl residue can abolish the ability of the peptides to block type IV collagenolytic activity.

These results can be integrated in a unifying hypothesis for the structure of the latent collagenase gene family enzymes and their activation. The zymogen forms are the result of the proenzyme segment containing the conserved sequence MRKPRCGN(V)PDV interacting with the enzyme active site to block catalytic activity. This interaction is stabilized through coordination of the zinc atom with the unpaired sulfhydryl side chain of the cysteinyl residue. Thus, any agent which disturbs the cysteinyl-metal atom coordination can result in enzyme activation and subsequent autocatalytic removal of the proenzyme fragment. This can be accomplished by reagents which would directly compete for the metal atom-sulfhydryl coordination, such as the organomercurial reagents. It might also be accomplished by chaotropic agents which would disturb the conformation of the proenzyme fragment surrounding the critical cysteinyl residue resulting in disruption of the metal atom coordination. Nonproteolytic tissue activators such as that described by Tyree et al., 1981 Archiv. Biochem. Biophys. 208, 440-443) may also activate these enzymes by a similar mechanism of induced conformational rearrangement, as has been proposed.

An additional preferred embodiment of the present invention is exemplified by the propeptide sequence 1-80 of the type IV procollagenase enzyme, which contains the intrinsic inhibitor sequence RKPRC incorporating an unpaired cysteine residue. In addition, the amino terminal end of this 80 amino acid peptide contains an internal disulfide bond, and this peptide also contains a tumor cell surface binding site. The 80mer peptide, made either by synthetic chemistry or by recombinant means, for example, may therefore have advantages as an inhibitor for at least three reasons. Firstly, its inhibitory activity on a molar basis can be higher than a peptide because the secondary structure of the inhibitory sequence is accurately reproduced. Secondly the recombinant 80mer protein has greater stability (longer half life) in vivo due to the presence of the disulfide bond at the amino terminus. Thirdly, since the 80mer contains a cell binding site it can target to the surface of the tumor cells where the deleterious proteolysis event is taking place. FIG. 13 illustrates the nucleotide sequence of the portion of a human cDNA clone for human type IV procollagenase which encodes the 80 amino acid sequence of the amino terminal peptide that is cleaved from human type IV procollagenase upon activation. A DNA segment having this nucleotide sequence (or any other sequence specifying the same amino acid sequence according to the universal genetic code) can be used in various recombinant protein production systems to produce the 80mer for use as an inhibitor of matrix metalloproteinases. Alternatively, the DNA segment having this nucleotide sequence, which is derived from the human genome, can be delivered into a mammal as part of a recombinant expression vector to provide an internal genetic source of production of the 80mer inhibitor of matrix metalloproteinases Methods Culture Methods Human A2058 melanoma cells were grown to 80% confluence in DMEM with 10% fetal bovine serum. The media was then replaced with serum-free DMEM and the culture continued for 24 hours. The serum-free conditioned media was collected and concentrated by ultrafiltration (Amicon YM 30 membrane) prior to storage at −20° C.

Purification of Type IV Procollagenase

Type IV procollagenase was purified directly from human A2058 melanoma cell concentrated conditioned media by gelatin-Sepharose (Sigma) affinity chromatography in 0.05M Tris HCl, 0.005M $CaCl_2$, 0.5M NaCl, pH 7.6 buffer (TCS buffer) containing 0.02% Brij 35 (Sigma). The enzyme was eluted using TCS buffer containing 0.02% Brij plus 7% dimethyl sulfoxide. The sample was then concentrated and stored in the same buffer at −70° C. until use. Type IV procollagenase was further purified by reverse-phase HPLC prior to amino acid sequence analysis on a Dionex A1400 system equipped with a 0.46×10 cm RP300 column (Pierce Co.) equilibrated in 0.1% trifluoroacetic acid. The column was eluted with a linear gradient to a 60% acetonitrile.

Preparation of Antibodies to Synthetic Peptides

The peptides used in the immunization procedures were synthesized on a Biosearch 9600 peptide synthesizer. Antibodies were prepared and purified as described for Example 3. The antibody preparations were characterized by ELISA using a commercial ELISA kit (Kirkegaard and Perry Laboratories) Immulon 2 plates (Dynatech, Inc.) as shown in FIG. 3.

Activation of Type IV Procollagenase by Organomercurials

Stock solutions of 0.01M p-APMA in 0.05N NaOH were prepared fresh daily. Proenzyme samples were incubated with a final concentration 0.5 or 1.0 mM p-APMA for varying times (0–16 hours) at 37° C. Following incubation, the samples were analyzed directly by $NaDodSO_4$-PAGE on 9% acrylamide gels containing 0.1% gelatin (gelatin zymogram). Alternatively, the samples were run on 9% $NaDodSO_4$-PAGE and electroblotted onto Immobilon P membranes (Millipore).

Assays for Type IV Collagenolytic Activity

Type IV collagenase activity was assayed in the presence of inhibitory peptides as described for Example 1. The substrate used was ³H-propionylated, human type IV collagen (New England Nuclear). The reactions were carried out at 28° C. for 4 to 16 hours.

EXAMPLE 3

Antibodies Recognizing Metalloproteinase Peptides

Synthetic peptides corresponding to a series of domains of Type IV procollagenase extending from the amino terminus (residues 1-17), to an internal domain near the carboxy terminus (residues 472-490) (FIG. 1, Table 3) were used as antigens to generate affinity purified polyclonal antibodies which recognized their respective domains on the native type IV procollagenase.

TABLE 3

Synthetic Peptides Used as Antigens for Matrix Metalloproteinase (N->C)

1. Ala-Pro-Ser-Pro-Ile-Ile-Lys-Phe-Pro-Gly-Asp-Ala-Pro-Lys-Thr-Asp-Lys
2. Glu-Leu-Ala-Val-Gln-Tyr-Leu-Asn-Thr-Phe-Tyr-Gly-Cys-Pro-Lys
3. Asn-Thr-Phe-Tyr-Gly-Cys-Pro-Lys-Glu-Ser-Cys-Asn-Leu-Phe-Val-Leu-Lys
4. Glu-Ser-Cys-Asn-Leu-Phe-Val-Leu-Lys-Asp-Thr-Leu-Lys-Met-Gln-Lys
5. Phe-Phe-Gly-Leu-Pro-Gln-Thr-Gly-Asp-Leu-Asp-Gln-Asn-Thr-Ile-Glu
6. Thr-Met-Arg-Lys-Pro-Arg-Cys-Gly-Asn-Pro-Asp-Val-Ala-Asn
7. Thr-Met-Arg-Lys-Pro-Arg-Cys-Gly-Asn-Pro-Asp-Val-Ala-Asn-Tyr-Asn-Phe-Phe-Pro-Arg-Lys-Pro-Lys
8. Arg-Lys-Pro-Arg-Cys-Gly-Asn
9. Asn-Pro-Asp-Val-Ala-Asn-Tyr-Asn-Phe-Phe-Pro-Arg-Lys-Pro-Lys-Trp-Asp-Lys-Asn-Gln
10. Met-Ile-Asn-Phe-Gly-Arg-Trp-Glu-His-Gly
11. Lys-Tyr-Gly-Phe-Cys-Pro-Glu-Thr-Ala
12. Met-Ser-Thr-Val-Gly-Gly-Asn-Ser-Glu-Gly-Ala
13. Met-Trp-Cys-Ala-Thr-Thr-Ala-Asn-Tyr-Asp-Asp-Arg-Lys-Trp-Gly-Phe-Cys-Pro-Asp-Gln-Gly-Tyr-Ser-Leu
14. Val-Ala-Ala-His-Glu-Phe-Gly-His-Ala-Met-Gly-Leu-Glu-His-Ser-Gln
15. Ala-Ala-His-Glu
16. Asp-Lys-Pro-Met-Gly-Pro-Leu-Leu-Val-Ala-Thr-Phe-Trp-Pro-Glu-Leu-Pro-Glu-Lys.

Enzyme-linked immunosorbentassays (ELISA) were used to demonstrate that antibody binding to solid phase synthetic peptides could be competed by solution phase peptides, and that each affinity purified antibody was monospecific (FIG. 3). Western immunoblotting studies of the time course of organomercurial activation process demonstrated that the antibodies recognized the solid phase enzyme in purified form, or among a complex mixture of proteins secreted by tumor cells in culture (FIG. 3). Western blotting also indicated a direct loss Of the amino terminal domain (residues 1-80) during the conversion to the lower molecular weight form (FIG. 7). Thus, antibodies which recognize peptide domains in the first 1-80 amino terminal residues could be used to distinguish the latent from the active form of the enzyme. Antibodies recognizing peptides in Table 3 were demonstrated to be useful in solid phase or solution phase direct or competition immunoassays to detect type IV collagenase antigen in human serum and human urine. Such body fluid assays are useful for diagnosis of localized or metastatic cancer. The anti-peptide antibodies were also demonstrated to be useful in the diagnosis of human colon carcinoma by immunohistology (Table 4).

Table 4 is a summary of an immunohistology case review of human colon cancer cases demonstrating that antibodies directed against the peptides in Table 3 can be used to identify enzyme antigen associated with malignant tumor cells.

TABLE 4

TYPE IV COLLAGENASE IMMUNOREACTIVITY ANTI-PEPTIDE ANTIBODY

| TISSUE | POSITIVE/TOTAL |
|---|---|
| NORMAL GASTRIC MUCOSA | 0/20 |
| GASTRIC CARCINOMA | |
| CONFINED TO MUCOSA | 18/20* |
| INVADING THE SUBMUCOSA | 20/20** |
| INVADING FULL THICKNESS | 20/20** |
| NORMAL COLORECTAL MUCOSA | 0/10 |
| NEOPLASTIC COLONIC POLYPS | 1/10 |
| COLORECTAL CARCINOMA | |
| CONFINED TO MUCOSA | 1/10* |
| INVADING THE SUBMUCOSA | 8/10** |
| INVADING FULL THICKNESS | 18/20** |

*10-30% TUMOR CELL REACTIVITY
**50-80% TUMOR CELL REACTIVITY

Methods

Protein Peptides

Synthesis of the protein peptides was carried out on a Biosearch Model 9600 peptide synthesizer using standard Merrifield solid-phase peptide synthesis protocols. The primary sequence synthesized was VAAHEFG-HAMGLEHSQ which corresponds exactly to residues 371-386 in human type IV collagenase as shown in FIG. 1. The three His and the two Glu residues were replaced in various combinations with Ala residues and the effect of this substitution on the type IV collagenase and zymogram gelatinase activity was investigated.

Preparation of Antipeptide Antibodies

The preparation of antipeptide antibodies utilized the following steps.

Conjugation of the peptide to BSA: To make the peptide antigenic, it must be covalently bound to BSA or another antigenic protein. To 2 mg of peptide is added one ml of PBS, and to 6 mg of BSA is added 4 ml of PBS. These solutions are combined and 5 ml of 0.25% glutaraldehyde solution is then added to this mixture. The resulting solution is stirred at room temperature for 4 hours, then dialyzed against 1 liter of PBS overnight at room temperature. The next day, the solution is concentrated to 6 ml and dispensed in 1 ml aliquots for immunization.

Immunization of rabbits: To ensure as much as possible high titers of antibody, all immunizations should be carried out using complete Freund's adjuvant. For the first two injections, 1 ml of BSA-peptide conjugate and 1 ml of CFA are emulsified and two rabbits are injected s.c. on the back with 1 ml of emulsion at approximately 30 sites. After the second injection, 0.5 ml of conjugate solution is diluted with 0.5 ml of PBS when making the emulsion. Immunizations are done every two weeks; a bleeding is done prior to immunization, and against the weeks between injections, beginning with the third or fourth injection.

Preparation of peptide antibody affinity resin: Once the anti-peptide antibody serum becomes available, the next step is to do an affinity purification step. In the first step, a peptide affinity resin is prepared. Approximately 10-12 ml of Affi-Gel 10 (BioRad Co.) is quickly washed 3X with 40 ml of Cold PBS, and resuspended in cold PBS to give a total volume of about 20 ml. At the same time, 2 mg of peptide is dissolved in 1 ml of PBS, and added to the Affi-Gel suspension with immediate mixing. The resulting mixture is gently agitated overnight in the cold. The next day, sufficient 1M Tris HCl, pH 8.0, is added to make a 0.2M solution, and the gel agitated an additional 4 hours in the cold. The gel is ready for antibody adsorption after washing 3× with 40 ml of PBS.

Affinity purification of antibody: The antibody-containing serum is heated at 56° C. for 30 minutes, cooled and mixed with the peptide resin, which was previously allowed to settle and had excess PBS poured off. After gentle agitation overnight in the cold, the gel suspension is poured into a column and washed with two gel volumes of cold 1M acetic acid followed by 1 gel volume of PBS. The antibody eluate is taken to approximately pH 7.0 with 6N NaOH, and the resulting solution is diaflo (YM-30) concentrated to about 5 ml, with buffer exchanged to PBS.

Coupling antibody to resin: The procedure is much the same as above, except that antibody coupling is allowed to go only 1 hour before Tris is added to stop the reaction and cap up unused active sites.

Immunoassays: Enzyme-linked immunosorbent assays, Western blotting studies, and immunohistology was conducted using standardized, well-accepted methods.

Polyclonal or monoclonal antibodies to the peptides chosen and purified as described above can be labeled with suitable radioactive, enzymatic or fluorescent labels by conventional methods, which should be apparent to those skilled in the art. Immunologic assays employing peptides and antibodies described herein can be applied to biologic samples of any type including body fluids, tissue extracts, or tissue sections, using conventional immunologic methods and with the aid of unlabeled, bound, or unbound antibodies or peptides. Antibodies or peptides can be coupled to suitable solid phase supports such as microtiter wells. The described anti-peptide antibodies for type IV collagenase have significant advantages over antibodies made against native whole enzyme (Tryggvason, K. and Liotta, L. A. U.S. Pat. No. 4,677,058). Firstly, they recognize specific domains unique to type IV collagenase which are not homologous to other prevalent metalloproteinases. This is non-obvious and overcomes a significant problem in that large proportions of the amino acid sequence of type IV collagenase is highly homologous or even identical with other metalloproteinases as shown in FIG. 2. Antibodies made against the peptides in Table 3 distinguish type IV collagenase from other metalloproteinases and furthermore can distinguish activated from latent enzyme. This latter feature is very important because pathologic situations could exist in which the ratio of latent to activated enzyme is the determining factor in disease diagnosis or prognosis.

The foregoing invention has been described in some detail for purposes of clarity and understanding. It will also be obvious to one skilled in the art that various changes and combinations in form and detail can be made without departing from the scope of the invention. In particular, it is obvious to those skilled in the art that modifications in the flanking sequences of the peptide inhibitors described herein may alter Stability, activity, or specificity toward individual members of the metalloproteinase family. For example, the choice of the specific sequences to the left of the activation associated cleavage site indicated in FIG. 10 may cause the inhibitor to preferentially inhibit stromelysin or type I collagenase compared to type IV collagenase. This is because this region of the sequence shows some variability between the different matrix metalloproteinase types. It is further obvious that certain substitutions of amino acid choices in non-critical regions of the peptides may not significantly alter the inhibitory properties of the peptide. In the case of synthetic peptides to be used as immunogens or antigens for antibodies specific for a matrix metalloproteinase, one skilled in the art will understand that a unique amino acid sequence in terms of recognition by an antibody binding site consists of a sequence of from four to six amino acids which is not known to exist in another protein in the environment for which the antibody is to be used (e.g., human biological specimens. Finally, it is known in the art that recombinant protein peptides can have activity comparable to natural peptides or synthetic peptides. The embodiments of the invention can therefore obviously be produced using suitable DNA segments inserted into appropriate expression vectors as well by synthetic peptide chemistry or isolation from natural sources where available. In any case, the peptides of this invention may be purified according to a variety of standard methods well known in the art.

For purposes of completing the background description and present disclosure, each of the published articles, patents and patent applications heretofore identified in this specification are hereby incorporated by reference into the specification.

What is claimed is:

1. A purified peptide having the amino acid sequence APSPIIKFPGDVAPKTDK.

2. A purified peptide having the amino acid sequence DKPMGPLLVATFWPELPEK.

3. A composition of matter which comprises said peptide of claim 1 in an amount sufficient to elicit an immune response together with a pharmaceutically acceptable carrier.

4. The composition of matter of claim 3 in which said peptide is covalently linked to an immunogenic carrier protein.

5. A composition of matter which comprises said peptide of claim 2 in an amount sufficient to elicit an immune response together with a pharmaceutically acceptable carrier.

6. The composition of matter of claim 5 in which said peptide is covalently linked to an immunogenic carrier protein.

* * * * *